United States Patent [19]
Kelliher et al.

[11] Patent Number: 5,088,620
[45] Date of Patent: Feb. 18, 1992

[54] GLOVE DISPENSER

[76] Inventors: Richard Kelliher, 18-B Meadow Way, Scotts Valley, Calif. 95066; Martin Schutt, 9-13 Creekside Pl., Manteca, Calif. 95336

[21] Appl. No.: 693,806

[22] Filed: Apr. 30, 1991

[51] Int. Cl.⁵ .............................................. B65H 1/08
[52] U.S. Cl. ..................................... 221/59; 221/279; 221/307; 206/278
[58] Field of Search ....................... 221/33, 56, 59, 60, 221/45, 307, 279; 206/278; 220/404

[56] References Cited

U.S. PATENT DOCUMENTS

| | | | |
|---|---|---|---|
| 3,150,808 | 9/1964 | Vensel | 221/59 |
| 3,486,657 | 12/1969 | Blatz | 221/59 |
| 4,002,276 | 1/1977 | Poncy et al. | 206/278 |
| 4,155,494 | 5/1979 | Poncy et al. | 206/278 |
| 4,199,076 | 4/1980 | Brown | 221/59 |
| 4,773,532 | 9/1988 | Stephenson | 206/278 |
| 4,844,293 | 7/1989 | McLaughlin | 221/34 |
| 4,925,058 | 5/1990 | Ozawa | 221/279 |

FOREIGN PATENT DOCUMENTS 305236  3/1989  European Pat. Off. ............. 221/34

Primary Examiner—H. Grant Skeggs
Attorney, Agent, or Firm—Jeffrey A. Hall

[57] ABSTRACT

A dispenser for gloves comprising a tubular body having a first end and a second end and having a spring disposed therein. The spring is secured to a moveable disc shaped member. A flexible mammillated shaped element having a first end and a second end is secured to the disc shaped member at the first end and secures a plurality of gloves therein. The second end of the mammillated member is secured to the second end of said tubular body. A top element which slideably fits over the second end of the tubular body has an opening therein and a diaphragm element having an aperture therein is secured over said opening. The spring urges the disc shaped member against the flexible mammillated shaped member containing the gloves allowing removal of one glove at a time from the aperture in the diaphragm element.

20 Claims, 2 Drawing Sheets

GLOVE DISPENSER

BACKGROUND OF THE INVENTION

1. Field of the Invention

This invention relates to glove dispensers, especially to glove dispensers for disposable thin plastic gloves where the gloves may be retrieved by the user one at a time.

2. Description of Prior Art

The use of disposable gloves is widespread and diverse. Many professional occupations, including ambulance, fire, police, medical, dental, laboratory personnel, and many others, use such disposable gloves for a wide variety of uses and applications. A major limitation to expanding the use and availability of such gloves resides in the manner in which they have been packaged for use and distribution to the ultimate consumer.

Frequently, such gloves are needed either one at a time or in pairs by the ultimate user. Furthermore, in many situations it is highly desirable for a single glove to be retrieved without contaminating other gloves in the packaging. It would also be highly desirable to have a ready means of transporting gloves in a dispenser which could conveniently be used in emergency situations frequently encountered by the ambulance, fire, police and other public safety workers, in hospital emergency rooms, laboratories, and the like, and a dispenser which is easily transported or stored in laboratories or professional offices.

Heretofore a wide variety of glove dispensers have been proposed and implemented.

One such dispenser is disclosed in U.S. Pat. No. 4,844,293 issued to McLaughlin where a box-like, generally rectangular enclosure is provided for housing a removably mounted packet containing gloves. The enclosure was provided with a front window and a removable cover or cap. The packet of gloves comprised a pair of faces connected to one another and having a configuration conforming to the shape of the gloves in an open palm condition. The enclosure included means to support the gloves in a parallel relationship being biased towards the front window of the enclosure. Although such dispenser provided a means to dispense gloves one at a time, it was significantly limited by necessitating the use of a packet of gloves having the gloves arranged in a generally planer condition prior to use.

Another genre of glove dispenser is disclosed in U.S. Pat. No. 4,773,532 issued to Stephenson in which a package of flattened sterile surgical gloves was provided in a roll form. The roll of gloves consisted of a continuous spirally wound sheet having uniformly spaced parallel transverse tear lines. The gloves were attached by adhesive to the sheet. Although useful in some limited applications such dispensing system suffered significant limitations due to the inability of the user to mount the gloves on such sheet, that is, such sheet had to be purchased preformed, with the gloves adhered thereto by adhesive. Furthermore, such roll dispensers resulted in a greater overall cost to the user in that for each glove dispensed a sheet of plastic and adhesive was also dispensed along with the glove, which then had to be discarded as a waste product of this dispensing system.

Another dispensing system is disclosed in U.S. Pat. No. 4,677,697 issued to Hayes where disposable gloves were manufactured within two sheets of joined plastic sheets sealed by a sheet sealing treatment. A fastener cut was provided on the sheets and a tie strip extended along the outside of the cuff portion of the glove to aid in turning the glove inside out to form a container to capture an object to be disposed within, the glove was then tied, and the object disposed. An aroma bubble was also located on the outside of the glove and was intended to burst and thereby deodorize the contents tied and sealed within the glove.

Still other approaches for dispensing objects are seen in U.S. Pat. No. 4,658,983 issued to Suttles, and U.S. Pat. No. 4,199,076 issued to Brown. Both patents disclose cup dispensers of generally tubular construction. The Brown patent disclose a dispenser having a helical spring which urges a plate towards a cavity allowing removal of one cup at a time.

U.S. Pat. No. 3,150,808 issued to Vensel discloses a dispenser for rolled paper in which a paper roll was loaded into a cylindrical tube shaped dispenser having a spring operably disposed therein. Such dispenser provided some utility for rolled paper dispensing but was not useful for more flexible objects such as gloves. Moreover, such apparatus did not function adequately except in combination with a specially designed paper roll adapted to be dispensed therefrom which was operably biased by the internal spring.

Moreover, such dispensing systems were impaired by failing to provide protection against casual tampering, the elements of weather, or environmental contaminants, thereby significantly hindering the use thereof in many applications.

More users therefore would find it highly desirable to have a glove dispenser which can easily, conveniently, and reliably dispense one glove at a time, which does not require using pre-rolled or specially manufactured gloves, which is useful in a wide variety of situations, and which may be manufactured in a low cost manner so as to provide the ultimate user with all of the above advantages in an economically reasonable dispensing system.

SUMMARY OF THE INVENTION

The glove dispenser of the present invention provides a tubular body element having a first end and a second end, said first end having a bottom element attached thereto. A compression spring having a first end and a second end is operably secured at said first end to the bottom element. A disc shaped member having a centrally positioned aperture is secured to the second end of the compression spring so as to urge the disc towards the second end of said tubular body. A flexible mammilliated shaped element having a first end and a second end is secured at said first end to the disc shaped member, and secured at said second end to said second end of the tubular body. A top element having an opening therein and adapted to be slideably received by said second end of said tubular body. A diaphragm having an aperture therethrough and operably coupled to said top element, thereby providing access to gloves removably secured with the mammilliated shaped element. A retaining ring is secured around said top element and said diaphragm to secure the top element and the diaphragm to the tubular body.

A primary object of the present invention is to provide a glove dispenser for easily, reliably, and conveniently dispensing gloves one at a time.

Another object of the invention is to provide a glove dispenser which is portable, and which may be mounted in any position while automatically urging gloves remaining within the mammilliated shaped element to the top end of the dispenser after removal of each glove.

It is also an object of invention to provide a glove dispenser which is easy to refill with gloves, and which is capable of dispensing a wide variety of gloves in a convenient and reliable fashion.

A still further object of the invention is to provide a glove dispenser which is useful in a wide variety of applications such as ambulances, police cars, fire vehicles, hospital emergency rooms and labs, as well as in the offices of doctors and dentists, that is convenient to use and protects against tampering, the elements of weather, and environmental contaminants.

A still further object of the invention is to provide a glove dispenser which is of simple construction and inexpensive to manufacture.

These and other objects and advantages of the glove dispenser of the present disclosure will be apparent to those skilled in the art from the following description of a preferred embodiment, claims, and accompanying drawings.

Drawing Reference Numerals

Figure 1:
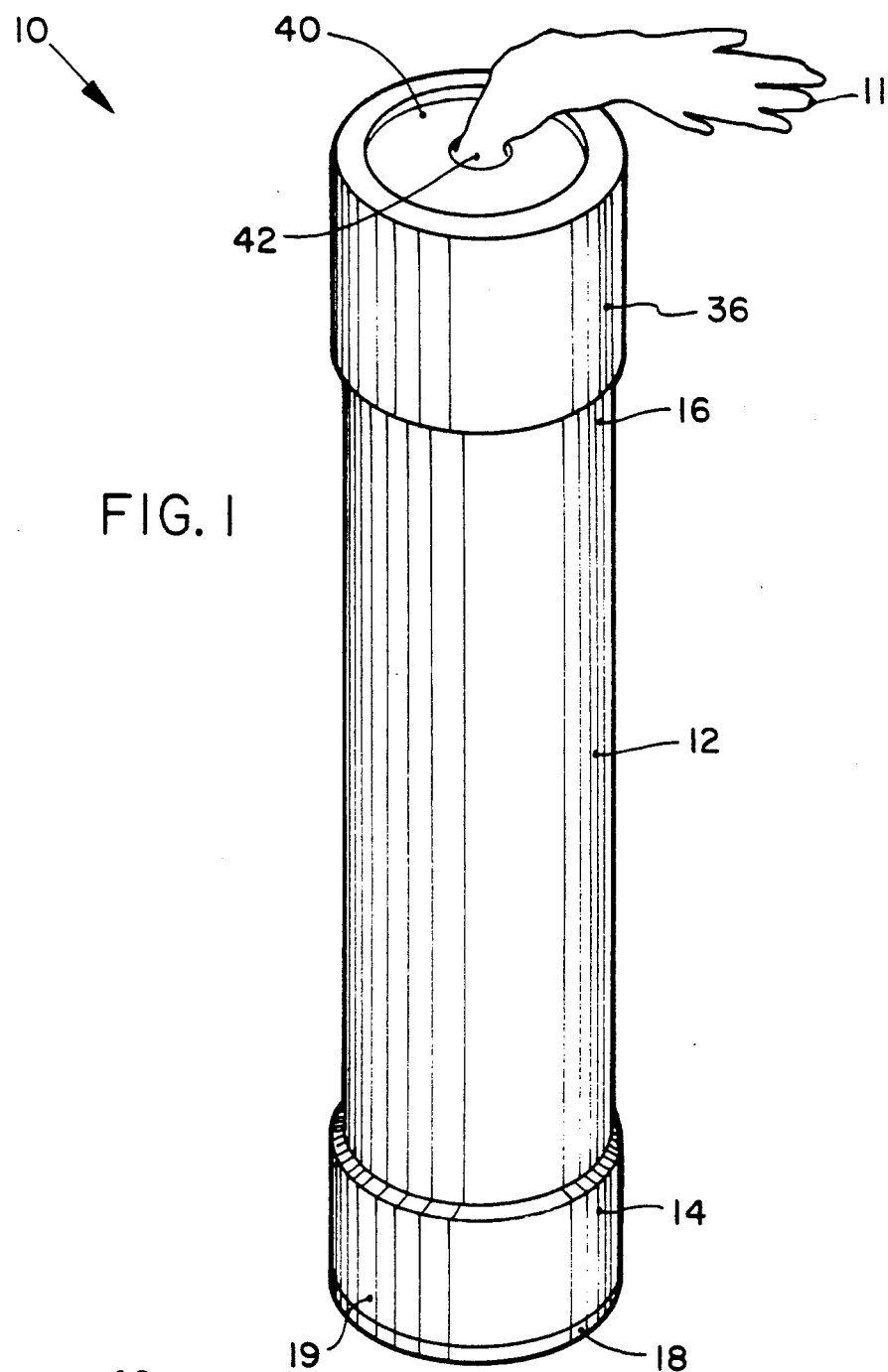
FIG. 1 shows a front perspective view of the glove dispenser, according to the invention.

10: glove dispenser
11: glove
12: tubular body
14: bottom end of tubular body
16: top end of tubular body
18: bottom element
19: adhesive layer
20: spring
21: bottom end of spring 20
22: disc shaped element
23: top end of spring 20
24: aperture in 22
26: flexible mammilliated shaped element
28: knot
30: bottom end of mammilliated shaped element
32: top end of mammilliated shaped element
34: adhesive layer
35: open cavity in mammilliated shaped element
36: top element
38: aperture in top element 36
40: diaphragm
41: adhesive layer
42: aperture in diaphragm 40
44: retaining ring
46: adhesive layer

DETAILED DESCRIPTION OF THE PREFERRED EMBODIMENT

FIG. 1 shows a glove dispenser 10 dispensing gloves 11 according to the preferred embodiment of the invention. The glove dispenser 10 comprises a tubular body 12 having a bottom or first end 14 and a top or second end 16. A bottom element 18 is preferably secured to tubular body 12 by adhesives 19. Tubular body 12 is preferably composed of a durable resistant plastic, but may be otherwise.

Figure 2:
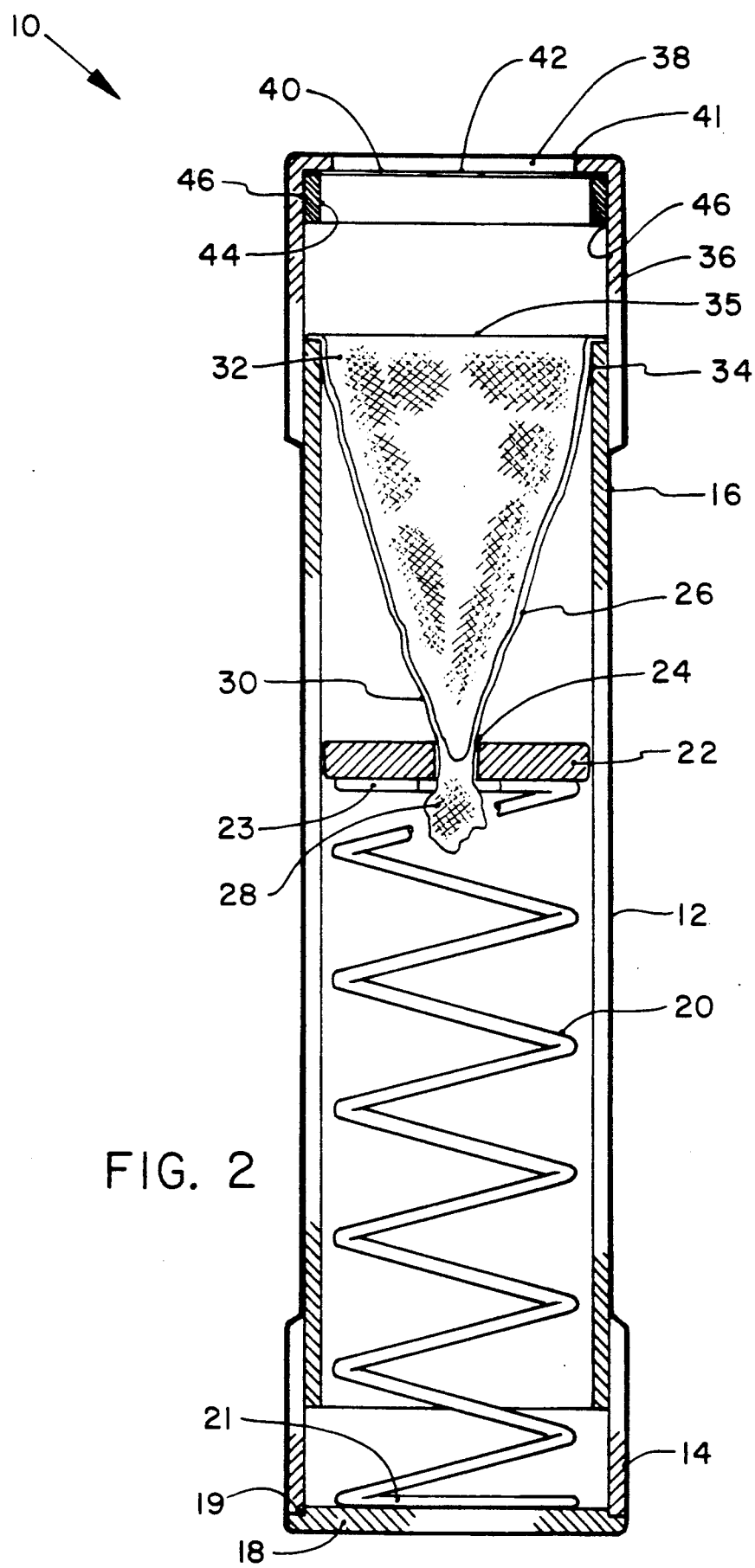
FIG. 2 shows a side sectional view of such glove dispenser, according to the invention.

Referring now to FIG. 2 a spring 20, preferably a compression spring, having a bottom or first end 21 and top or second end 23, is operably disposed within tubular boy 12. First end 21 of spring 20 is preferably secured to bottom element 14 by adhesives, however, other conventional fastening means such as screws, clips, or staples may also be used. The second end 23 of spring 20 is operably coupled to a disc shaped element 22 having an aperture 24 therethrough. Disc shaped element 22 is freely moveable within tubular body 12 and is urged towards the second end 16 of tubular body 12 by spring 20. Disc shaped element 22 is preferably composed of a durable resistant plastic, but may alternatively be composed of urethane, metal, or any other durable resistant material.

A flexible, preferably mammilliated shaped element 26 having a bottom or first end 30 and a top or second end 32, is secured to disc shaped member 22. The mammilliated shaped element is preferably composed of nylon, but may alternatively be composed of any flexible material such as, plastic, urethane, or the like. In the preferred embodiment, a knot 28 is placed in mammilliated shaped element 26 on the spring side of disc element 22 preventing slippage of mammilliated shaped element 26 through aperture 24. Alternatively a pin, clip, adhesive, or any other mechanical fastening means known in the art may be utilized. The second end 32 of mammilliated shaped element 26, is secured to the second end 16 of tubular body 12. In the preferred embodiment, mammilliated shaped element 26 is draped over the sides of tubular element 12 and secured by adhesives 34 creating an open cavity 35 in mammilliated element 26 for holding gloves 11. Alternatively, mammilliated shaped element 26 may be secured to the inner surface of tubular body 12 by adhesives or other conventional fastening means.

A top element 36 having aperture 38 is adapted to be slideably received by end 16 of tubular body 12. A diaphragm 40 having a preferably centrally positioned aperture 42 therethrough is preferably secured to top element 36 by adhesive layer 41 or other conventional fastening means, with retaining ring 44 secured to top element 36 with adhesives 46. Diaphragm 40 is preferably composed of a flexible plastic. Alternatively, diaphragm 40 may be composed of urethane, felt, or other durable, flexible material. Retaining ring 44 is preferably secured within top element 36 and diaphragm 40 by adhesives 46.

Figure 3:
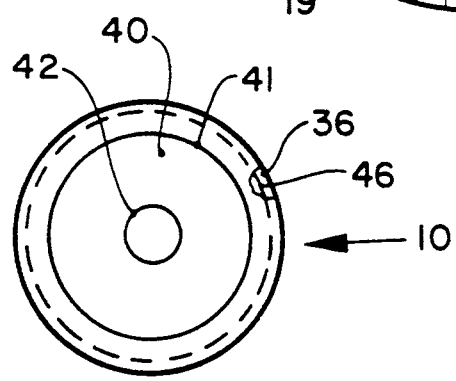
FIG. 3 shows a top view of such glove dispenser.
Figure 4:
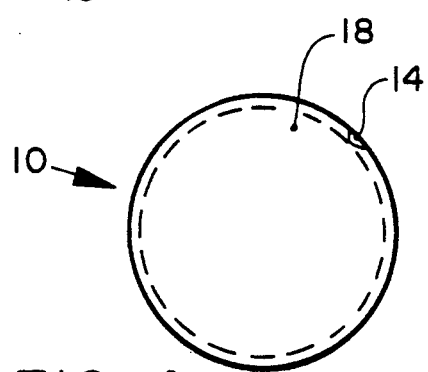
FIG. 4 shows a bottom view of such glove dispenser.

Referring now to FIG. 3, a top view of glove dispenser 10 is illustrated showing diaphragm 40 with aperture 42. Diaphragm 40 is preferably secured to top element 36 by retaining ring 44 and by adhesives 46. In the preferred embodiment retaining ring 44 is composed of a durable resistant plastic, but may be otherwise. FIG. 4 illustrates a bottom view of glove dispenser 10.

In operation and use the glove dispenser 10 of the instant invention conveniently and reliably dispenses gloves singly from the dispenser. Glove dispenser 10 is preferably used for dispensing commercially available latex/rubber gloves in widespread use in the medical and emergency services professions.

Glove dispenser 10 can be mounted in any position, for example, vertically or horizontally, and operates by the user manually pulling a glove out of aperture 42 in diaphragm 40. Spring 20 urges disc shaped element 22 towards the top end 16 of tubular body 12 and thereby pushes the remaining gloves in mammilliated shaped element 26 to the top end of dispenser 10 and thereby readily available for retrieval.

To reload dispenser 10 with gloves, the user simply places gloves through aperture 42 in diaphragm 40. Alternatively, if dispenser 10 is constructed with a removable top element 36, top element 36 is removed and gloves placed in cavity 35 of mammilliated shaped element 26. Further, the design of dispenser 10 allows for the convenient use of pre-loaded glove cartridges within the dispenser 10 if desired.

The glove dispenser 10 of the present invention is useful in a wide variety of applications including use in emergency vehicles, such as police cars, ambulances, and fire response vehicles, food processing applications, hospitals, and laboratories. Additionally, glove dispenser 10 may be conveniently used in the offices of doctors, dentists, and other health care professionals, as well as horticultural, biological, and other scientific research.

While the above description contains many specificities these should not be construed as limitations on the scope of the invention, but merely as exemplifications of preferred embodiments thereof. Those skilled in the art will envision many other possible variations are within its scope. For example, the shape and dimensions of body 12 could be varied, or various materials could be substituted for those described herein. Various means could be utilized to secure mammilliated shaped element 26 to disc 22, or alternative diaphragm configurations could be substituted for those described. Glove dispenser 10 could be manufactured to conform to a wide variety of holding brackets or could be provided as a free standing unit. Accordingly, the scope of the invention should be determined by the appended claims and their legal equivalents, and not by the examples which have been given.

We claim:

1. A glove dispenser for dispensing disposable gloves, comprising:
   a tubular body having a first end and a second end, said first end having a bottom element secured thereto,
   a spring having a first end and a second end, said first end being operably secured to said bottom element,
   a disc shaped member having an aperture therethrough secured to said second end of said spring and adapted to slideably fit within said tubular body,
   a mammilliated shaped element having a first end and a second end, said first end of said mammilliated element is secured to said disc shaped member, and said second end is secured to said second end of said tubular member,
   a top element adapted to be slideably received by said second end of said tubular body,
   a diaphragm element having an aperture therethrough and operably coupled to said top element thereby providing access to gloves removably secured within said mammilliated shaped element, and
   means for retaining said diaphragm element to said top element.

2. The glove dispenser of claim 1 wherein said bottom element is secured to said tubular body by adhesives.

3. The glove dispenser of claim 1 wherein said spring is a compression spring.

4. The glove dispenser of claim 1 wherein said disc shaped member is composed of a plastic.

5. The glove dispenser of claim 1 wherein said mammilliated element is compose of nylon.

6. The glove dispenser of claim 1 wherein said mammilliated element is composed of a fabric.

7. The glove dispenser of claim 1 wherein said mammilliated element is composed of plastic.

8. The glove dispenser of claim 1 wherein said diaphragm element is composed of plastic.

9. The glove dispenser of claim 1 wherein said diaphragm element is composed of latex rubber.

10. The glove dispenser of claim 1 wherein said second end of said mammilliated element is secured to said second end of said tubular body by adhesives.

11. The glove dispenser of claim 1 wherein said means for retaining said diaphragm element to said top element comprises a retaining ring.

12. The glove dispenser of claim 11 wherein said retaining ring is secured to said diaphragm element and said top element by adhesives.

13. A portable glove dispenser for dispensing gloves, comprising:
   an elongated body having a first end and a second end, said first end having a bottom element attached thereto,
   a compression spring having a first end and a second end, said first end being operably secured to said bottom element,
   a disc shaped member having a centrally positioned aperture, said disc shaped member being secured to said second end of said compression spring, said member being adapted to slideably fit within said elongated body,
   a flexible mammilliated shaped element having a first end and a second end, said first end of said mammilliated shaped element being secured to said disc shaped member, and secured at said second end to said second end of said elongated body,
   a top element having an opening therein and adapted to be slideably received by said second end of said elongated body,
   a diaphragm having an aperture therethrough and operably coupled to said top element, thereby providing access to gloves removably secured within said mammilliated shaped element, and
   means for securing said top element to said diaphragm element.

14. The glove dispenser of claim 13 wherein said bottom element is secured to said elongated body by adhesives.

15. The glove dispenser of claim 13 wherein said disc shaped member is composed of a plastic.

16. The glove dispenser of claim 13 wherein said mammilliated element is composed of nylon.

17. The glove dispenser of claim 13 wherein said diaphragm element is composed of latex rubber.

18. The glove dispenser of claim 13 wherein said second end of said mammilliated element is secured to said second end of said elongated body by adhesives.

19. The glove dispenser of claim 13 wherein said means for securing said top element to said diaphragm element comprises a retaining ring.

20. The glove dispenser of claim 19 wherein said retaining ring is secured to said diaphragm element and said top element by adhesives.

* * * * *